United States Patent [19]
Kuracina

[11] Patent Number: 5,304,151
[45] Date of Patent: Apr. 19, 1994

[54] ADD-ON FAIL-SAFE SAFETY CAP FOR PASSIVE SLIDING-SLEEVE NEEDLE PROTECTORS

[75] Inventor: Thomas C. Kuracina, Ojai, Calif.

[73] Assignee: InjectiMed, Inc., Ventura, Calif.

[21] Appl. No.: 51,020

[22] Filed: Apr. 22, 1993

Related U.S. Application Data

[63] Continuation-in-part of Ser. No. 49,260, Apr. 16, 1993.

[51] Int. Cl.⁵ .................................. A61M 5/32
[52] U.S. Cl. ........................... 604/198; 604/263
[58] Field of Search ............. 604/198, 192, 187, 263, 604/110

[56] References Cited

U.S. PATENT DOCUMENTS

| | | | |
|---|---|---|---|
| 4,863,434 | 9/1989 | Bayless | 604/198 |
| 5,026,356 | 6/1991 | Smith | 604/192 |
| 5,059,184 | 10/1991 | Dyke | 604/198 |
| 5,176,656 | 1/1993 | Bayless | 604/198 |

Primary Examiner—John D. Yasko
Attorney, Agent, or Firm—Donald A. Streck

[57] ABSTRACT

An add-on fail-safe safety cap for mounting on a retracting protective sleeve for a hypodermic needle. An annular collar is concentrically positioned around the sleeve adjacent its outer end. There is at least one tip shield carried by the collar with each tip shield having an arm portion hingedly attached to the collar on an inner end, an activating tab portion adjacent the inner end, and a tip protector portion at an outer end of the arm portion. Each tip shield is hingedly moveable between a retracted position with its tip protector out of a path of movement of the tip portion of the needle and a protecting position with its tip protector covering the tip portion of the needle. The tip protector is biased to the retracted position whereby when the locking collar is retracted from the locked position the tip protector is in the retracted position and when the locking collar is in the locked position the tip protector is pushed to the retracted position by the locking collar pushing on the activating tab portion.

15 Claims, 3 Drawing Sheets

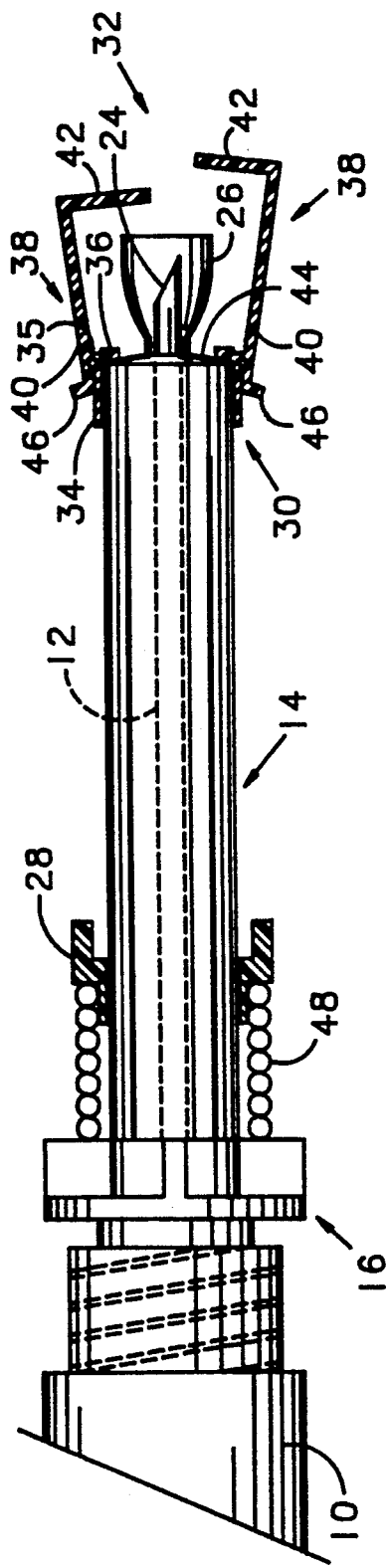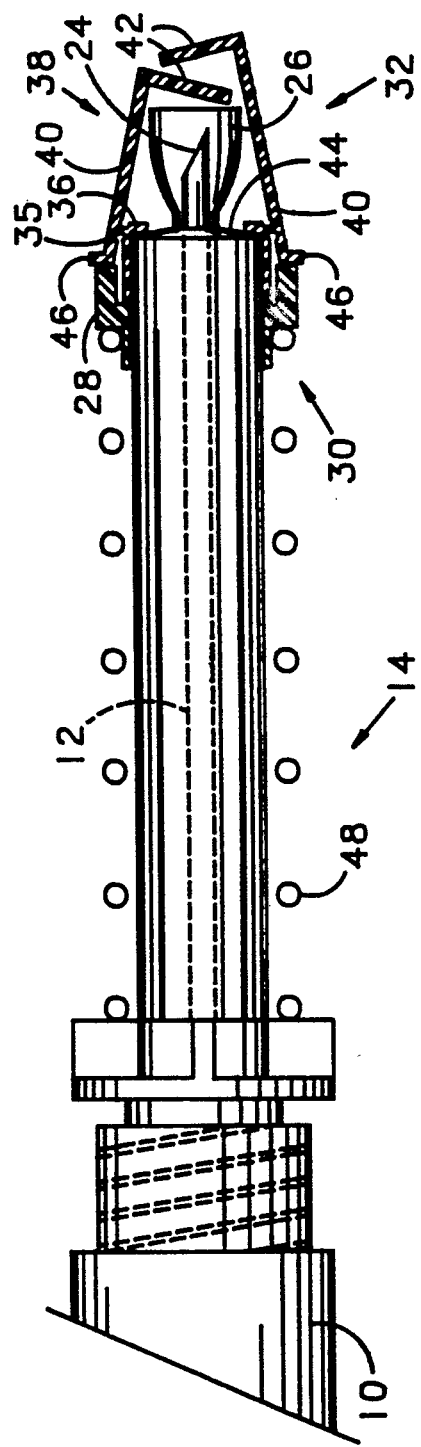

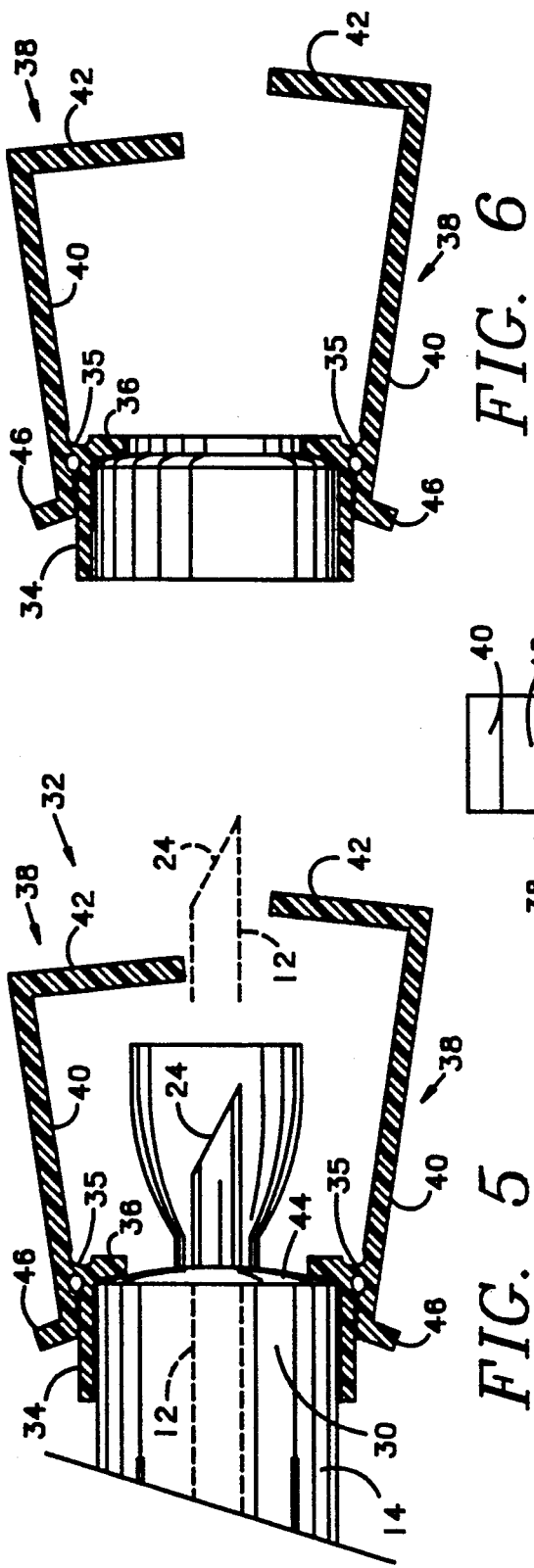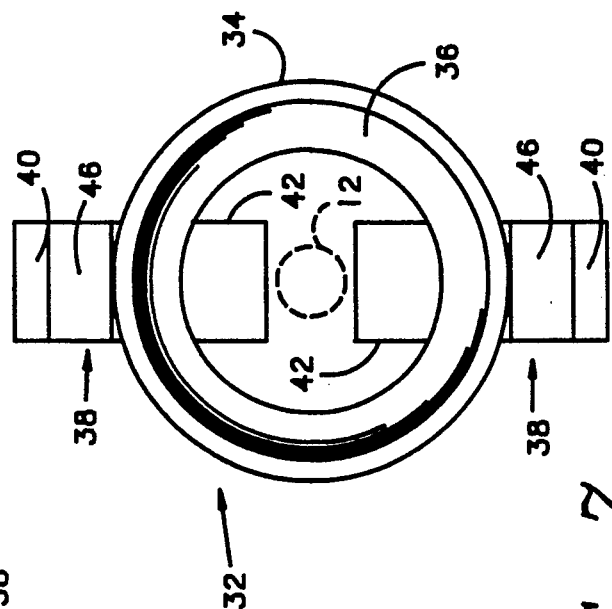
FIG. 6
FIG. 5
FIG. 7

ADD-ON FAIL-SAFE SAFETY CAP FOR PASSIVE SLIDING-SLEEVE NEEDLE PROTECTORS

BACKGROUND OF THE INVENTION

This application is a continuation-in-part of patent application Ser. No. 049,260, filed Apr. 16, 1993.

This invention relates to safety hypodermic syringes intended to prevent accidental needle stick and, more particularly, to an add-on fail-safe safety cap for mounting on a retracting protective sleeve for a hypodermic needle having an outer end with a bore therethrough though which a tip portion of the needle passes and further having a spring-biased locking collar which moves to a locked position adjacent the outer end whereby to add further protection against accidental needle sticks comprising, an annular collar concentrically positioned around the sleeve adjacent the outer end; and, at least one tip shield carried by the annular collar, each tip shield having an arm portion hingedly attached to the collar on an inner end, an activating tab portion adjacent the inner end, and a tip protector portion at an outer end of the arm portion, each tip shield being hingedly moveable between a retracted position with its tip protector out of a path of movement of the tip portion of the needle and a protecting position with its tip protector covering the tip portion of the needle; biasing means for biasing the tip protector to the retracted position whereby when the locking collar is retracted from the locked position the tip protector is in the retracted position and when the locking collar is in the locked position the tip protector is pushed to the retracted position by the locking collar pushing on the activating tab portion; and, stop means associated with the collar for positioning the collar on the outer end of the sleeve adjacent the bore.

In the above-referenced patent application, ways in which a secondary fail-safe shield could be incorporated into a passive sliding-sleeve needle protector were disclosed for reasons set forth in detail therein which will not be restated in this application in the interest of simplicity and the avoidance of redundancy. The same is true for the prior art disclosures made therein, which are incorporated herein by reference.

It is the object of this invention to provide a way of adding a similar capability to existing sliding-sleeve needle protectors.

SUMMARY

The foregoing object has been achieved by the add-on fail-safe safety cap of the present invention for mounting on a retracting protective sleeve for a hypodermic needle having an outer end with a bore therethrough though which a tip portion of the needle passes and further having a spring-biased locking collar which moves to a locked position adjacent the outer end whereby to add further protection against accidental needle sticks comprising, an annular collar concentrically positioned around the sleeve adjacent the outer end; a pair of tip shields carried by the annular collar, each tip shield having an arm portion hingedly attached to the collar on an inner end, an activating tab portion adjacent the inner end, and a tip protector portion at an outer end of the arm portion, each tip shield being hingedly moveable between a retracted position with its tip protector out of a path of movement of the tip portion of the needle and a protecting position with its tip protector covering the tip portion of the needle, the pair of tip shields being disposed 180° from one another with associated arm portions being of unequal length whereby associated tip protector portions overlap one another when in the protecting position; biasing means for biasing the tip protector to the retracted position whereby when the locking collar is retracted from the locked position the tip protector is in the retracted position and when the locking collar is in the locked position the tip protector is pushed to the retracted position by the locking collar pushing on the activating tab portion; and, stop means associated with the collar for positioning the collar on the outer end of the sleeve adjacent the bore, the stop means comprising a stop ring contacting an end wall of the sleeve having the bore therethrough; wherein, the collar and the pair of tip shields are of unitary construction of a tough, pierce-resistant plastic; and, the biasing means comprises a living hinge formed in the plastic whereby the arm portions are self-biasing from a restorative force of the plastic in the living hinge.

Preferably, each tip protector portion forms an angle of less than 90° with an associated arm portion.

DESCRIPTION OF THE DRAWINGS

FIG. 3 is a side view drawing of the sliding sleeve passive needle protector of FIG. 1 with the safety cap of this invention attached to the end of the sleeve, with the sleeve extended in its needle-protecting position, and with the locking collar retracted so that the sleeve can be retracted.

FIG. 4 is a side view drawing of the sliding sleeve passive needle protector of FIG. 1 with the safety cap of this invention attached to the end of the sleeve, with the sleeve extended in its needle-protecting position, and with the locking collar in its front sleeve-locking preventing the sleeve from being retracted and further urging the protective tabs of the safety cap over the needle tip.

FIG. 5 is an enlarged drawing of the front portion of FIG. 3.

FIG. 6 is a cutaway drawing of just the safety cap of FIG. 5.

FIG. 7 is a sleeve-end view of the safety cap of FIG. 6.

DESCRIPTION OF THE PREFERRED EMBODIMENT

Figure 1:
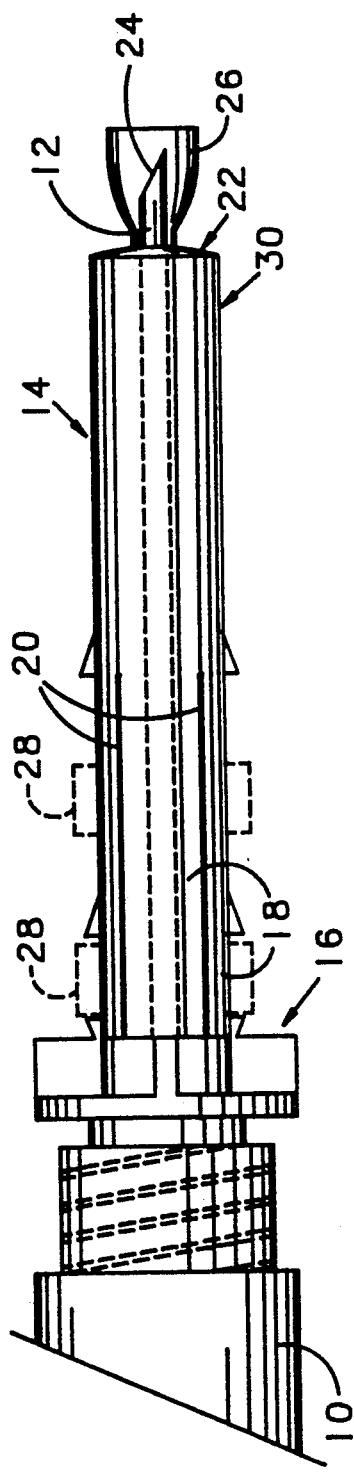
FIG. 1 is a side view drawing of a prior art sliding sleeve passive needle protector with the sleeve extended in its needle-protecting position.
Figure 2:
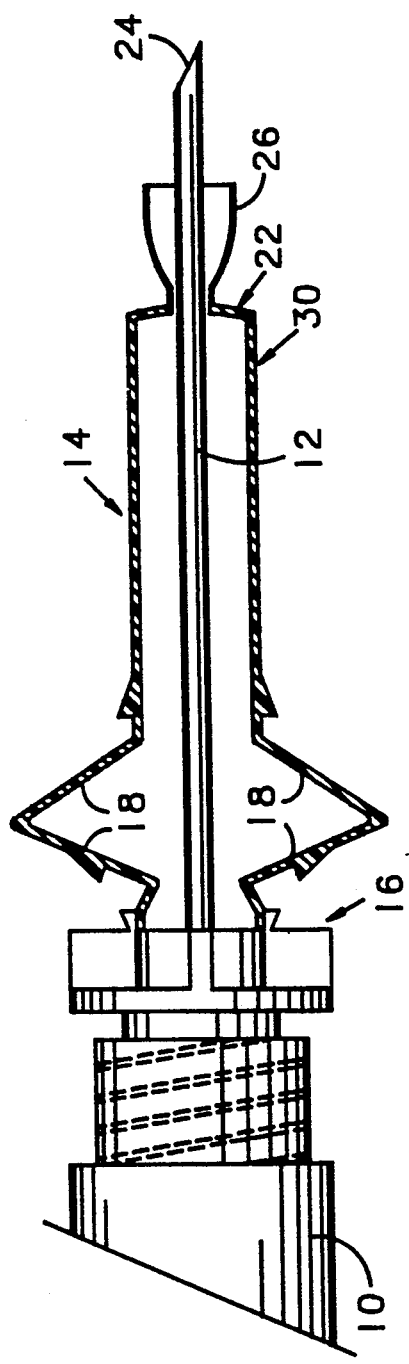
FIG. 2 is a side view drawing of the prior art sliding sleeve passive needle protector of FIG. 1 with the sleeve retracted to expose the needle tip for use.

The environment as wherein the present invention is applicable is shown in FIGS. 1 and 2. A syringe 10 having a needle 12 extending therefrom has the needle covered by a retracting protective sleeve 14 which is mounted on a hub 16 on the end of the syringe 10. The sleeve 14 contains a plurality of longitudinal slats 18 formed by slits 20 through the sidewalls of the sleeve 14. The needle 12 passes through a bore 22 in the closed outer end of the sleeve 14 and, in the preferred embodiment, the tip 24 of the needle 12 is contained within a thin-walled viewing bell 26. For use, a locking collar shown ghosted as 28 in FIG. 1 is retracted against the front biasing force of a helical spring (not shown) so that the slats 18 can bend and retract the front portion 30 to expose the needle tip 24 as depicted in FIG. 2. Once the syringe 10 has been used on a patient, the sleeve 14 extends to its position of FIG. 1 from the self-biasing force of the plastic of the slats 18 and the spring forces the locking collar 28 to a front position preventing the slats 18 from easily bending. It is from excessive compressive forces that can deform the front portion 30 and its components and/or the slats 18 that additional protection is needed and for which the present invention is intended.

The add-on protective cap 32 of the present invention is shown in FIGS. 3-7. The "cap" 32 is actually a cylindrical collar 34 having a stop ring 36 (or a plurality of radially spaced stop tabs) around its outer periphery and hingedly carrying at least one L-shaped tip shield 38. While metal could be used, it is preferred that the cap 32 be of unitary construction and molded of one of the tough, pierce-resistant plastics well known to those skilled in the art. Other shapes could, of course, be employed if desired. The preferred number of such tip shields 38 is two as shown. Each tip shield 38 comprises an arm portion 40 carrying a tip protector 42 on its outer end with the inner end being attached to the collar 34 with a self-biasing so-called "living hinge" 35 which biases the tip protector 42 to its retracted position of FIGS. 3 and 5-7. The tip protectors 42 could be concave facing the needle tip 24, if desired. Note that one arm portion 40 is longer than the other so that the tip protectors 42 will overlap in their closed and protective position as depicted in FIG. 4 rather than hitting one another and preventing proper deployment of the tip protectors. If a concave tip protector is not employed, the tip protectors 42 should preferably form less than a 90° angle with the arms 40 so that the needle tip 24 will be forced into the angle between the tip protector 42 and its arm 40 in the event of a longitudinal blow thereto instead of moving outward and slipping off the end of the tip protector.

As best seen from the enlarged drawing of FIG. 5, the cap 32 is added to a standard sleeve 14 by forcing the collar 34 over the front portion 30 until the stop ring 36 contacts the front end 44 of the sleeve 14. The arms 40 are sized to place the tip protectors 42 in their proper position when the collar 34 is thus positioned. The collar 34 can be a friction fit over the front portion 30 or, preferably, is adhesive or heat bonded to the plastic of the sleeve 14.

While one tip shield 38 can be employed and two as shown are preferred, those skilled in the art will readily recognize that configurations of three or four radially equally spaced tip shields 38 could be employed to further protect the needle tip 24. On the one hand, obviously the more layers of pierce-resistant plastic that are over the tip 24 of the needle 12, the less chance there is for an accidental needle stick. On the other hand, the more tip protectors 42 that must overlap, the greater the chance that they will interfere with one another and the further in front of the viewing bell 26 the stack of tip protectors 42 will project. There is also the issue of what will happen to the tip protectors 42 when and if they come in contact with the patient's skin. Two tip protectors 42 can be positioned on opposite sides of the needle 12 rather than above and below as pictured. That way, the needle tip 24 can be viewed between the tip protectors 42 and the tip protectors 42 should simply move out of the way when and if they contact the patient's skin.

As a final note, it is preferred that each arm 40 have a generally vertical activation tab 46 located adjacent the living hinge 35. Preferably, the distance between the activation tab 46 and the living hinge 35 is far smaller than the distance between the living hinge 35 and the tip protector 42. Thus, the tip protector 42 moves a great distance in response to a small movement of the activation tab 46. As depicted in FIG. 4, when the locking collar 28 is released and moves forward from the force of the spring 48, the locking collar 28 pushes the activation tabs 46 forward thus moving the tip protectors 42 down to their protective position.

Wherefore, having thus described the present invention, what is claimed is:

1. In a retracting protective sleeve for a hypodermic needle having an outer end with a bore therethrough though which a tip portion of the needle passes and further having a spring-biased locking collar which moves to a locked position adjacent said outer end, an add-on fail-safe safety cap comprising:
   a) an annular collar concentrically positioned around the sleeve adjacent the outer end;
   b) at least one tip shield carried by said annular collar, each said tip shield having an arm portion hingedly attached to said collar on an inner end, an activating tab portion adjacent said inner end, and a tip protector portion at an outer end of said arm portion, each said tip shield being hingedly moveable between a retracted position with its said tip protector out of a path of movement of the tip portion of the needle and a protecting position with its said tip protector covering the tip portion of the needle; and,
   c) biasing means for biasing said tip protector to said retracted position whereby when the locking collar is retracted from the locked position said tip protector is in said retracted position and when the locking collar is in the locked position said tip protector is pushed to said retracted position by the locking collar pushing on said activating tab portion.

2. The add-on fail-safe safety cap for a retracting protective sleeve for a hypodermic needle of claim 1 wherein:
   said collar has stop means for positioning said collar on the outer end of the sleeve adjacent the bore.

3. The add-on fail-safe safety cap for a retracting protective sleeve for a hypodermic needle of claim 2 wherein:
   said stop means comprises a stop ring contacting an end wall of the sleeve having the bore therethrough.

4. The add-on fail-safe safety cap for a retracting protective sleeve for a hypodermic needle of claim 1 wherein:
   said collar and each said tip shield are of unitary construction of a tough, pierce-resistant plastic.

5. The add-on fail-safe safety cap for a retracting protective sleeve for a hypodermic needle of claim 4 wherein:
   said biasing means comprises a living hinge formed in said plastic whereby said arm portion is self-biasing from a restorative force of said plastic in said living hinge.

6. The add-on fail-safe safety cap for a retracting protective sleeve for a hypodermic needle of claim 1 wherein:

there are a pair of said tip shields disposed 180° from one another with associated said arm portions being of unequal length whereby associated tip protector portions overlap one another when in said protecting position.

7. The add-on fail-safe safety cap for a retracting protective sleeve for a hypodermic needle of claim 1 wherein:
each tip protector portion forms an angle of less than 90° with an associated arm portion.

8. An add-on fail-safe safety cap for mounting on a retracting protective sleeve for a hypodermic needle having an outer end with a bore therethrough though which a tip portion of the needle passes and further having a spring-biased locking collar which moves to a locked position adjacent said outer end whereby to add further protection against accidental needle sticks comprising:
a) an annular collar concentrically positioned around the sleeve adjacent the outer end;
b) at least one tip shield carried by said annular collar, each said tip shield having an arm portion hingedly attached to said collar on an inner end, an activating tab portion adjacent said inner end, and a tip protector portion at an outer end of said arm portion, each said tip shield being hingedly moveable between a retracted position with its said tip protector out of a path of movement of the tip portion of the needle and a protecting position with its said tip protector covering the tip portion of the needle;
c) biasing means for biasing said tip protector to said retracted position whereby when the locking collar is retracted from the locked position said tip protector is in said retracted position and when the locking collar is in the locked position said tip protector is pushed to said retracted position by the locking collar pushing on said activating tab portion; and,
d) stop means associated with said collar for positioning said collar on the outer end of the sleeve adjacent the bore.

9. The add-on fail-safe safety cap for a retracting protective sleeve for a hypodermic needle of claim 8 wherein:
said stop means comprises a stop ring contacting an end wall of the sleeve having the bore therethrough.

10. The add-on fail-safe safety cap for a retracting protective sleeve for a hypodermic needle of claim 8 wherein:
said collar and each said tip shield are of unitary construction of a tough, pierce-resistant plastic.

11. The add-on fail-safe safety cap for a retracting protective sleeve for a hypodermic needle of claim 10 wherein:
said biasing means comprises a living hinge formed in said plastic whereby said arm portion is self-biasing from a restorative force of said plastic in said living hinge.

12. The add-on fail-safe safety cap for a retracting protective sleeve for a hypodermic needle of claim 8 wherein:
there are a pair of said tip shields disposed 180° from one another with associated said arm portions being of unequal length whereby associated tip protector portions overlap one another when in said protecting position.

13. The add-on fail-safe safety cap for a retracting protective sleeve for a hypodermic needle of claim 8 wherein:
each tip protector portion forms an angle of less than 90° with an associated arm portion.

14. An add-on fail-safe safety cap for mounting on a retracting protective sleeve for a hypodermic needle having an outer end with a bore therethrough though which a tip portion of the needle passes and further having a spring-biased locking collar which moves to a locked position adjacent said outer end whereby to add further protection against accidental needle sticks comprising:
a) an annular collar concentrically positioned around the sleeve adjacent the outer end;
b) a pair of tip shields carried by said annular collar, each said tip shield having an arm portion hingedly attached to said collar on an inner end, an activating tab portion adjacent said inner end, and a tip protector portion at an outer end of said arm portion, each said tip shield being hingedly moveable between a retracted position with its said tip protector out of a path of movement of the tip portion of the needle and a protecting position with its said tip protector covering the tip portion of the needle, said pair of tip shields being disposed 180° from one another with associated said arm portions being of unequal length whereby associated tip protector portions overlap one another when in said protecting position;
c) biasing means for biasing said tip protector to said retracted position whereby when the locking collar is retracted from the locked position said tip protector is in said retracted position and when the locking collar is in the locked position said tip protector is pushed to said retracted position by the locking collar pushing on said activating tab portion; and,
d) stop means associated with said collar for positioning said collar on the outer end of the sleeve adjacent the bore, said stop means comprising a stop ring contacting an end wall of the sleeve having the bore therethrough; wherein,
e) said collar and said pair of tip shields are of unitary construction of a tough, pierce-resistant plastic; and,
f) said biasing means comprises a living hinge formed in said plastic whereby said arm portions are self-biasing from a restorative force of said plastic in said living hinge.

15. The add-on fail-safe safety cap for a retracting protective sleeve for a hypodermic needle of claim 14 wherein:
each tip protector portion forms an angle of less than 90 ° with an associated arm portion.

* * * * *